United States Patent [19]

Masson et al.

[11] 4,143,077

[45] Mar. 6, 1979

[54] DIARYLOXY-META-TERPHENYL DERIVATIVES, THEIR MANUFACTURE AND USES

[75] Inventors: Bernard Masson, Poisat; Guy Rabilloud; Bernard Sillion, both of Grenoble, all of France

[73] Assignee: Institut Francais du Petrole, Rueil-Malmaison, France

[21] Appl. No.: 831,447

[22] Filed: Sep. 8, 1977

[30] Foreign Application Priority Data

Sep. 8, 1976 [FR] France .................. 76 27213

[51] Int. Cl.$^2$ .................. C07C 43/20; C10M 1/20; C10M 3/14; C09K 50/00
[52] U.S. Cl. .................. 568/636; 252/52 R; 252/71
[58] Field of Search .................. 252/52 R, 71; 260/613 R, 612 R

[56] References Cited

U.S. PATENT DOCUMENTS

| | | | |
|---|---|---|---|
| 3,293,305 | 12/1966 | Hazeldine et al. | 260/612 R |
| 3,403,185 | 9/1968 | Nilsson et al. | 260/612 R |
| 3,426,076 | 2/1969 | Mertwoy et al. | 252/52 R |
| 3,535,387 | 10/1970 | Mertwoy et al. | 260/612 R |
| 3,598,861 | 8/1971 | Griot | 260/612 R |
| 3,600,445 | 8/1971 | Wirth et al. | 260/613 R |
| 3,704,277 | 11/1972 | Clark | 252/52 R |
| 3,741,974 | 6/1973 | Griot | 260/613 R |
| 3,860,661 | 1/1975 | Hammann et al. | 252/52 R |

*Primary Examiner*—Delbert E. Gantz
*Assistant Examiner*—Irving Vaughn
*Attorney, Agent, or Firm*—Millen & White

[57] ABSTRACT

New aromatic compounds with ether functions particularly useful as power transmission fluids and as lubricants withstanding high temperatures, containing at least a major proportion of a compound of the formula:

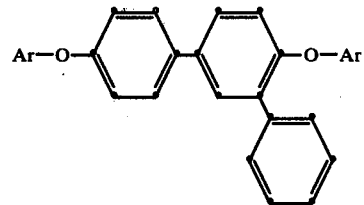

wherein each Ar is selected from phenyl and metaphenoxy phenyl and optionally a minor proportion of at least one compound selected from those complying with the general formulas:

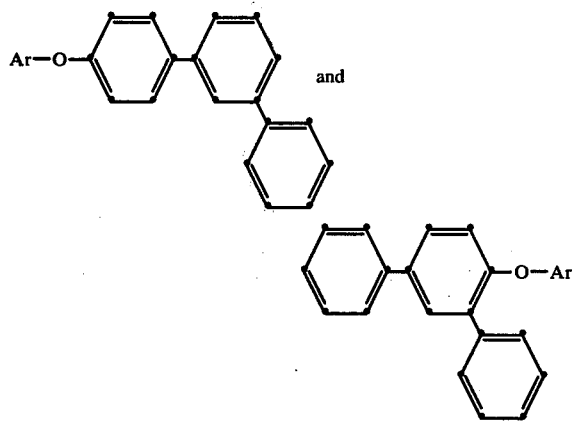

wherein Ar is defined as above.

7 Claims, No Drawings

DIARYLOXY-META-TERPHENYL DERIVATIVES, THEIR MANUFACTURE AND USES

The invention concerns new aromatic compounds with ethers functions, their manufacture and their uses.

In various fields, particularly in the supersonic aircraft, power transmission fluids and lubricants withstanding higher and higher temperatures are needed.

In addition to a good resistance to high temperatures, these fluids and lubricants must also have a good resistance to oxidation, a low volatility and as low as possible a pour point, while retaining a substantial viscosity at high temperature.

For these applications, there has been proposed, in the prior art, compounds of various chemical structures; however, it is observed that the systems of aliphatic type are not sufficiently stable and the compounds of aromatic structure are not easily melted. A satisfactory compromise seems to have been found by making use of compounds with polyphenyl-thio-ethers and polyphenyl-ethers groups. However, the synthesis of such compounds is time-consuming and expensive.

In addition, in order that the melting point of the considered compounds be as low as possible, it is necessary to make use of aromatic raw materials with meta substituents. However, generally such compounds are difficultly available.

There has now been discovered new aromatic compounds with ether functions which are much more easily available and which have all the required properties for being used with advantage as power transmission fluids or as lubricants at high temperatures, particularly in the field of supersonic aircraft.

The aromatic compounds with ether functions according to the invention comply with the general formula:

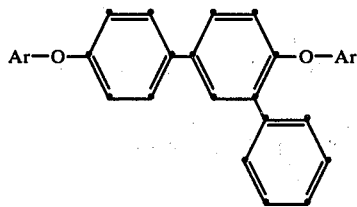

in which the radicals Ar, which may be identical or different, are monovalent aromatic rings of the phenyl type, optionally substituted in meta position by an aryloxy group. The compounds in which each radical Ar is a phenyl radical exhibit a series of properties which is quite satisfactory for the applications they are destined to.

The aromatic compounds with ether functions of the invention may be obtained by a process comprising the preparation of a 4,4'-dihalogenated derivative of meta-terphenyl, followed by the reaction of this dihalogenated derivative with an appropriate alkaline phenate.

The preparation of the 4,4'-dihalogenated derivative of meta-terphenyl is one of the original features of the invention. As a matter of fact, the conventional methods for halogenating meta-terphenyl do not lead to this type of product. In the case, for example, of bromination, the reaction of 1 mole of bromine with 1 mole of meta-terphenyl leads, as expected, to the mono-brominated derivative in 4' position, but the bromination with 2 moles of bromine results in the formation of a complex mixture of polybrominated compounds and not in the formation of 4,4'-dibromo-meta-terphenyl.

By the process of the invention, there can be obtained a selective disubstitution on positions 4 and 4' of the meta-terphenyl by first proceeding to the mono-bromination of meta-terphenyl, mainly to 4'-bromo-meta-terphenyl, followed with a mono-iodination, leading to the formation of 4-iodo-4'-bromo-meta-terphenyl, with a good yield.

A method which can be used, according to the invention, for the mono-bromination of meta-terphenyl is that described by Schmidt in Journal of Chemistry 25, 252 (1960). It consists of reacting bromine, in a proportion of about 15% less than the stoichiometrical amount, with a solution of meta-terphenyl in a halogenated solvent such as 1,2-dichloroethane, in the presence of iron and water, at ordinary temperature.

According to the invention, the operation is preferably conducted with a lower bromine insufficiency (for example about 5%); iron is used in a divided form (for example as filings); in order to improve the yield of 4'-bromo-terphenyl, the reaction is terminated by a heating step, for example at a temperature of about 40° C. for a few hours, e.g. 1 to 5 hours.

There is obtained a mixture consisting of a major part of 4'-bromo-m-terphenyl and which may also contain minor proportions of unreacted meta-terphenyl, 4-bromo-m-terphenyl, as well as small amounts of 4,4'-dibromo-m-terphenyl.

It is unecessary to separate 4'-bromo-m-terphenyl from this mixture, which is generally fed as such to the following step.

Iodination of the product issued from the bromination step may be effected by reaction of the latter with a convenient amount of molecular iodine, in the presence of an oxidizing agent. As oxidizing agent there is used, for example, silver sulfate, silver perchlorate, mercuric oxide, potassium persulfate, iodic acid, periodic acid, perchloric acid, o-iodo-anisole or even nitric acid.

There is obtained a mixture which contains a high proportion of 4-iodo-4'-bromo m-terphenyl, and which may also contain, particularly when the raw product from the bromination step has been subjected to iodination, various proportions of other 4,4'-dihalogenated derivatives (4,4'-diiodo and 4,4'-dibromo m-terphenyls) as well as mono-iodinated derivatives (mainly 4-iodo m-terphenyl).

The mono-halogenated (mono-iodinated) derivatives may be separated to a large extent from the mixture, for example by hexane extraction.

The resulting mixture may be used as such in the following step of condensation with the alkaline phenate.

It is also possible, if it is desired to obtain, at the end of the preparation, the 4-4'-diaryloxy m-terphenyl in a pure state (without monoaryloxy derivative) to proceed, at this stage, to the complete removal of the mono-halogenated derivatives.

The condensation of the product issued from the preceding step with the alkaline phenate (s), may be effected for example, in the conditions of the Ullmann's reaction. The halogenated product is contacted with at least one alkaline phenate of the general formula Ar—OM (where Ar is defined as precedingly and M is an alkaline metal), at a high temperature and in the presence of cupric oxide or a copper salt. The operation can be conducted in an organic solvent of polar type, as for example: pyridine, dimethyl-sulfoxide, dimethylacetamide, dimethylformamide, hexamethylphosphoramide, N-methyl pyrrolidone, diglyme, tetraglyme or still a polyglyme. The alkaline phenate is preferably sodium phenate.

In most cases, there is used a slight excess of alkaline phenate with respect to the number of halogen atoms (bromine and iodine) present in the halogenated product involved.

The diaryloxy compounds, obtained in some cases in admixture with a minor proportion of monoaryloxy compounds, are then thoroughly purified in order to remove all the impurities which would be liable to result in a chain degradation of the products, or in a too high volatility (thereby reducing to a large extent the advantage due to their stability at high temperature).

In order to purify the obtained aryloxy products, it is possible to proceed in one or more operations conducted according to methods known in the art, as follows:

Removal of all unreacted phenate traces by repeated washings of the organic phase containing aryloxy products, by means of an alkaline aqueous solution (sodium hydroxide solution, for example).

Removal of the light impurities by rectification under the highest possible vacuum.

Decoloration and tar removal by treatment on a mixture of activated earth and animal black, and decoloration and purification by chromatography over an alumina column after dissolution of the product in such a solvent as benzene or hexane.

The so-purified product essentially consists of 4-4'-diaryloxy m-terphenyl or of a mixture consisting of a major proportion of 4-4'-diaryloxy m-terphenyl and a minor proportion of 4-monoaryloxy-and 4'-monoaryloxy-m-terphenyl.

The 4,4'-diaryloxy m-terphenyls and their mixtures with mono-aryloxy compounds of meta-terphenyl, prepared and purified as above described, have melting properties, thermal stability and volatility which make them suitable for use as lubricants for turboengines.

The following examples illustrate the invention but must not be considered in any way as limiting the scope thereof.

EXAMPLE 1

Preparation of 4,4'-diphenoxy-m-terphenyl

Step (a) — In a 2 liters reactor provided with a propeller stirrer driven by a powerful motor, a thermometer, a refrigerant and a feeding funnel, there is placed: 460 g (2 moles) of m-terphenyl and 400 ml of 1,2-dichloroethane. After heating of the mixture to 80° C., there is added a few milliliters of bromine, iron filings and a few water drops. As soon as the vapors disappear, the reaction mixture is cooled down to room temperature. 304 g of bromine (1.9 moles, i.e. an insufficiency of 5%), are added very slowly, in 10 hours. In order to increase as much as possible the proportion of m-terphenyl participating to the reaction, the reaction mixture is subjected, after a 24 hours contact, to heating at 40° C. for 2 hours. The solution is then diluted with 2 liters of benzene, washed with a 10% aqueous solution of sodium carbonate, then with a 20% solution of sodium disulfite and finally with water up to neutrality. After evaporation of the solvent, there is obtained 553.9 g of a product which slowly crystallizes after a few days. The analyses by gaseous phase chromatography shows that this product is a mixture whose molar composition is as follows:

43.5 $10^{-2}$ moles of unreacted m-terphenyl: (23.1 mole %)

121.1 $10^{-2}$ moles of 4'-bromo m-terphenyl: (64.2 mole %)

17.0 $10^{-2}$ moles of 4-bromo m-terphenyl: (9.0 mole %)

7.0 $10^{-2}$ moles of 4,4'-dibromo m-terphenyl: (3.7 mole %)

Step (b) — In a 4 liters reactor equipped with a mechanical stirrer, a refrigerant and an inner thermometer, there is introduced: 475.5 g of the mixture obtained in step (a), i.e.: 37.3 $10^{-2}$ moles (85.8 g) of meta-terphenyl, 104 $10^{-2}$ moles (321.3 g) of 4'-bromo m-terphenyl, 14.6 $10^{-2}$ moles (45.1 g) of 4-bromo m-terphenyl and 6.0 $10^{-2}$ moles (23.3 g) of 4,4'-dibromo m-terphenyl. There is subsequently added 1980 ml of acetic acid, 396 ml of water and 59.4 ml of concentrated sulfuric acid and then, under stirring, 118.36 g (0.466 mole) of iodine and 53.124 g (0.233 mole) of periodic acid. After heating for 24 hours at 75° C., the product is extracted with 2 liters of chloroform. The organic phase is then washed with a 10% aqueous solution of sodium hydroxide, a 10% aqueous solution of disulfite and several times with water, up to neutrality. After evaporation, there is obtained 498.6 g of a very viscous product containing:

42.1 $10^{-2}$ moles (33.7%) of 4-iodo 4'-bromo m-terphenyl 13.1 $10^{-2}$ moles (10.5%) of 4,4'-diiodo m-terphenyl 11.9 $10^{-2}$ moles (9.5%) of 4,4'-dibromo m-terphenyl 44.1 $10^{-2}$ moles (35.3%) of 4-iodo m-terphenyl, and 13.8 $10^{-2}$ moles (11.0%) of 4'-iodo m-terphenyl Step (c) — A large portion of the monohalogenated products contained in the raw product may be separated by hexane addition under vigorous stirring. After filtration and washing three times with 250 ml of hexane, there is recovered 257.9 g of a solid (softening point: 104° C.), which contains:

33.1 $10^{-2}$ moles (54.6%) of 4-iodo 4'-bromo m-terphenyl 10.2 $10^{-2}$ moles (16.8%) of 4,4'-diiodo m-terphenyl 4.9 $10^{-2}$ moles (8.1%) of 4,4'-dibromo m-terphenyl 1.3 $10^{-2}$ moles (2.1%) of 4,4''-diiodo m-terphenyl 9.0 $10^{-2}$ moles (14.9%) of 4-iodo m-terphenyl, and 2.1 $10^{-2}$ moles (3.5%) of 4'-iodo m-terphenyl, which corresponds to about 1.10 gram-atom of halogen.

Step (d) — In a 2 liters reactor, provided with a paddle agitator, a feeding funnel, an inner temperature sensing means and a refrigerant, there is introduced, under strong scavenging with an inert gas: 28.83 g (1.25 gram-atom) of sodium and 100 ml of tetraglyme. Through the feeding funnel there is slowly added a solution of 122.95 g (1.31 mole) of phenol in 300 ml of tetraglyme. After a very exothermic initial reaction period, it becomes necessary to heat to 120° C. for 12 hours in order to obtain a complete reaction of the sodium. After addition of 8 g of CuO and heating to 190° C., a solution of the 257.9 g of halogenated derivatives from step (c) into 700 ml of tetraglyme is added in 1 hour 40 minutes. The reaction medium is then heated for 14 hours at 207° C., then for 28 hours 30 minutes at 215° C.

Step (e) — After filtration of the formed sodium bromide, the solution is diluted in 6 liters of benzene-ether mixture (50-50). The organic phase is washed with a 10% aqueous sodium hydroxide solution, then with $H_2O$ up to neutralization. There is obtained, after evaporation of the solvent, 250 g of a brown-maroon very viscous product. The purification is effected by passage over a column of neutral alumina (2 kg) with elution by a benzene-hexane mixture (50-50) (6 liters).

After evaporation of the solvent, there is separated 182.5 g of a light yellow coloured amorphous product. The last solvent traces and light products, if any, are removed by heating to 200° C. under $5 \times 10^{-3}$ mm Hg. There is thus obtained 167.5 g of a very slightly coloured, amorphous product, liquid at 60° C. The analysis by gaseous phase chromatography shows the presence of about 20% by mole of mono-phenoxy m-terphenyls and 80% by mole of 4,4'-diphenoxy m-terphenyl.

In the following examples, the main physical properties of the so-obtained purified mixture (referred to hereinunder as "polyphenoxy m-terphenyl"), are determined, as well as, by way of comparison, those of a polyphenylether available on the market.

EXAMPLE 2

Variation of the kinematic viscosity in relation with temperature

The values of kinematic viscosity, measured at increasing temperatures, are reported in Table I below.

TABLE I

| TEMPERATURE (°C.) | KINEMATIC VISCOSITY | |
|---|---|---|
| | Polyphenoxy m-terphenyl | Polyether of the market |
| 90 | 101 | 18.03 |
| 98.9 | 56 | 13.05 |
| 120 | 21.46 | 7.74 |
| 140 | 11.17 | 5.19 |
| 160 | 6.71 | 3.69 |
| 198 | 3.34 | 2.30 |

It is observed that the "polyphenoxy m-terphenyl" exhibits, at each temperature level, a much higher viscosity than that of the polyether of the market (at 198° C., in particular, the improvement is still of 55%).

EXAMPLE 3

Thermal stability

It is determined with the aid of a high pressure isoteniscope whereby it is possible to operate at constant volume and to measure the pressure variation in relation with temperature. Accordingly, to the decomposition temperature will correspond an abrupt pressure variation resulting in an abrupt change of the curve slope.

The obtained results are reported in Table 2 below.

TABLE 2

| | THERMAL DECOMPOSITION THRESHOLD |
|---|---|
| Polyphenoxy m-terphenyl | 530 |
| Polyphenyl-ether of the market | 550 |

EXAMPLE 4

Kinetics of weight loss by isothermal heating

The measurements are effected by means of a thermobalance; there is heated, in the presence of argon, 100 mg of sample at different temperature levels and the weight loss is recorded in relation with time.

By step heating to 350° C., the weight loss is 36% after 2 hours for "polyphenoxy m-terphenyl" instead of 62% for the sample of the market.

EXAMPLE 5

Kinetics of the weight loss by dynamic heating

The measurements are also effected with the aid of a thermobalance: there is heated 100 mg of sample in the presence of air, the temperature increase being regulated at 80° C./h and the weight loss is recorded versus time.

At 400° C., the weight loss of a sample of "polyphenoxy m-terphenyl" amounts to 54% whereas, for the product of the market, it amounts to 74%.

EXAMPLE 6

Oxidation-corrosion test

This oxidation-corrosion test is effected in the presence of an assembly of five metals: copper, steel, aluminum, titanium, silver. A sample of 20 g of the product to be tested is introduced in an elongate pyrex tube equipped with a refrigerant. After introduction of the metal assembly, air is introduced within the liquid at a rate of 0.2 l/h. The whole is then heated to 300° C. for 18 hours. At the end of the test, the modifications undergone by the sample are determined.

The obtained results are reported in Table 3 below.

TABLE 3

| | Polyphenoxy m-terphenyl | Polyphenyl ether |
|---|---|---|
| Aspect of the sample | clear | clear |
| After test | no deposit | no deposit |
| Coloration | Brown | Black |
| Viscosity variation (%) | | |
| at 60° C. | + 12% | + 5% |
| at 98.9° C. | + 2% | + 2% |
| Loss of volatile products % | 0.8 | 0.65 |
| Loss by weight mg/cm² Steel | 0 | − 0.16 |
| Copper | − 1.3 | − 0.80 |
| Aluminum | − 0.07 | − 0.37 |
| Silver | − 0.16 | − 0.77 |
| Titanium | − 0.04 | − 0.08 |

What we claim is:

1. A process for the preparation of a compound of the general formula:

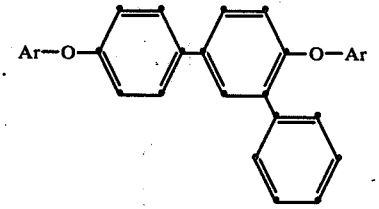

in which each Ar radical is an aromatic monovalent radical consisting of a phenyl radical or a metaphenoxy phenyl radical, comprising the successive steps of: (a) brominating metaterphenyl, mainly to 4'-bromo m-terphenyl; (b) iodinating the product issued from step (a) to a mixture containing a major proportion of dihalogenated derivatives, mainly 4-iodo 4'-bromo m-terphenyl, and a minor proportion of monohalogentated derivatives, mainly 4-iodo m-terphenyl; and (c) reacting the product issued from step (b) with at least one alkaline phenate of the general formula Ar—OM, wherein M is an alkaline metal.

2. A process according to claim 1 wherein between steps (b) and (c), there is provided the step (b') comprising removing the monohalogenated derivative from the mixture issued from step (b).

3. A process according to claim 1, wherein step (a) comprises reacting meta-terphenyl with a bromine amount 5% less than the stoichiometrical one, in a halogenated solvent, in the presence of iron and water, at room temperature and terminating the reaction by heating to a temperature of about 40° C. for 1 to 5 hours.

4. A process according to claim 1, wherein step (b) comprises reacting the product issued from step (a) with an appropriate amount of molecular iodine, in the presence of an oxidizing agent.

5. A process according to claim 2, comprising, in step (b), the removal of the monohalogenated derivatives by hexane extraction.

6. A process according to claim 1, comprising, in step (c), the reaction of the product issued from step (b) with an excess of alkaline phenate, by heating in the presence of cupric oxide or a copper salt.

7. A process according to claim 1, wherein the alkaline phenate involved in step (c) is sodium phenate.

* * * * *